US011059757B2

(12) United States Patent
Nouaille et al.

(10) Patent No.: US 11,059,757 B2
(45) Date of Patent: Jul. 13, 2021

(54) METHOD FOR PRODUCING ORGANIC MOLECULES FROM FERMENTABLE BIOMASS

(71) Applicant: Afyren, Saint Beauzire (FR)

(72) Inventors: Régis Nouaille, Cournon D'Auvergne (FR); Jérémy Pessiot, La Charite sur Loire (FR)

(73) Assignee: AFYREN, Saint Beauzire (FR)

(\*) Notice: Subject to any disclaimer, the term of this patent is extended or adjusted under 35 U.S.C. 154(b) by 44 days.

(21) Appl. No.: 15/327,524

(22) PCT Filed: Jul. 17, 2015

(86) PCT No.: PCT/FR2015/051967
§ 371 (c)(1),
(2) Date: Jan. 19, 2017

(87) PCT Pub. No.: WO2016/012701
PCT Pub. Date: Jan. 28, 2016

(65) Prior Publication Data
US 2017/0158572 A1    Jun. 8, 2017

(30) Foreign Application Priority Data

Jul. 25, 2014  (FR) .................................... 1457198

(51) Int. Cl.
| | | |
|---|---|---|
| C05F 1/00 | (2006.01) |
| C12M 1/107 | (2006.01) |
| C12P 5/02 | (2006.01) |
| C12P 39/00 | (2006.01) |
| C12P 7/52 | (2006.01) |
| C12P 7/40 | (2006.01) |
| C12M 1/00 | (2006.01) |
| C12P 7/54 | (2006.01) |
| C25B 3/00 | (2021.01) |
| C05F 1/02 | (2006.01) |
| C05F 9/00 | (2006.01) |
| C05F 9/02 | (2006.01) |

(52) U.S. Cl.
CPC .............. *C05F 1/005* (2013.01); *C05F 1/007* (2013.01); *C05F 1/02* (2013.01); *C05F 9/00* (2013.01); *C05F 9/02* (2013.01); *C12M 21/04* (2013.01); *C12M 29/20* (2013.01); *C12M 43/00* (2013.01); *C12M 99/00* (2013.01); *C12P 5/023* (2013.01); *C12P 7/40* (2013.01); *C12P 7/52* (2013.01); *C12P 7/54* (2013.01); *C12P 39/00* (2013.01); *C25B 3/00* (2013.01); *Y02A 40/20* (2018.01); *Y02E 50/30* (2013.01); *Y02P 20/145* (2015.11); *Y02W 30/40* (2015.05)

(58) Field of Classification Search
CPC .................................................... Y02A 40/203
See application file for complete search history.

(56) References Cited

U.S. PATENT DOCUMENTS

| | | | |
|---|---|---|---|
| 4,358,537 A | 11/1982 | Chynoweth | |
| 6,043,392 A * | 3/2000 | Holtzapple | ........... C07C 29/145 44/385 |
| 2013/0309740 A1 | 11/2013 | Yu | |

FOREIGN PATENT DOCUMENTS

| | | |
|---|---|---|
| WO | 9900512 | 1/1999 |
| WO | 2012170989 A2 | 12/2012 |
| WO | 2013033772 | 3/2013 |

OTHER PUBLICATIONS

English translation of International Preliminary Report on Patentability in PCT/FR2015/051967, dated Jan. 31, 2017, 11 pages.
English translation of International Search Report in PCT/FR2015/051967, dated Oct. 9, 2015, 4 pages.
English translation of Written Opinion of the International Searching Authority in PCT/FR2015/051967, dated Oct. 9, 2015, 10 pages.
Colon, et al., "On-line removal of volatile fatty acids from CELSS anaerobic bioreactor via nanofiltration", Life Support & Biosphere Science: International Journal of Earth Space, 2001, vol. 7, No. 4, pp. 291-299.

(Continued)

*Primary Examiner* — Bin Shen

(57) ABSTRACT

The process for producing organic molecules from fermentable biomass includes a step of anaerobic fermentation (5) producing volatile fatty acids (6), these precursors being transformed into final organic molecules by non-fermentation means. It also includes at least the following steps: a) extracting (9) at least one portion of the volatile fatty acids from the fermentation medium in such a way that the production of fermentation metabolites by the microorganisms (M) is not affected, and introducing a portion of the liquid phase (11) containing microorganisms from the extraction (9), b) synthesizing (13) organic molecules from the fermentation metabolites or from the volatile fatty acids extracted in step a)-c) continuing steps a) to b) until the final molecules are obtained, in terms of amount and quality. The invention also relates to an installation for implementing the process.

10 Claims, 1 Drawing Sheet

(56) References Cited

OTHER PUBLICATIONS

Pessiot, et al., "Fed-batch Anaerobic Valorization of Slaughterhouse By-products with Mesophilic Microbial Consortia Without Methane Production", Appl. Biochem. Biotechnol. Jan. 6, 2012, 17 pages.
Steinbusch, et al., "Biological formation of caproate and caprylate from acetate: fuel and chemical production from low grade biomass", Energy & Environmental Science, vol. 4, No. 1, Jan. 1, 2011, pp. 216-224.
Voulis, "Bioelectrochemical upgrading of volatile fatty acids", Masters dissertation, Faculty of Bioscience Engineering, Univ. of Ghent, 2012.

* cited by examiner

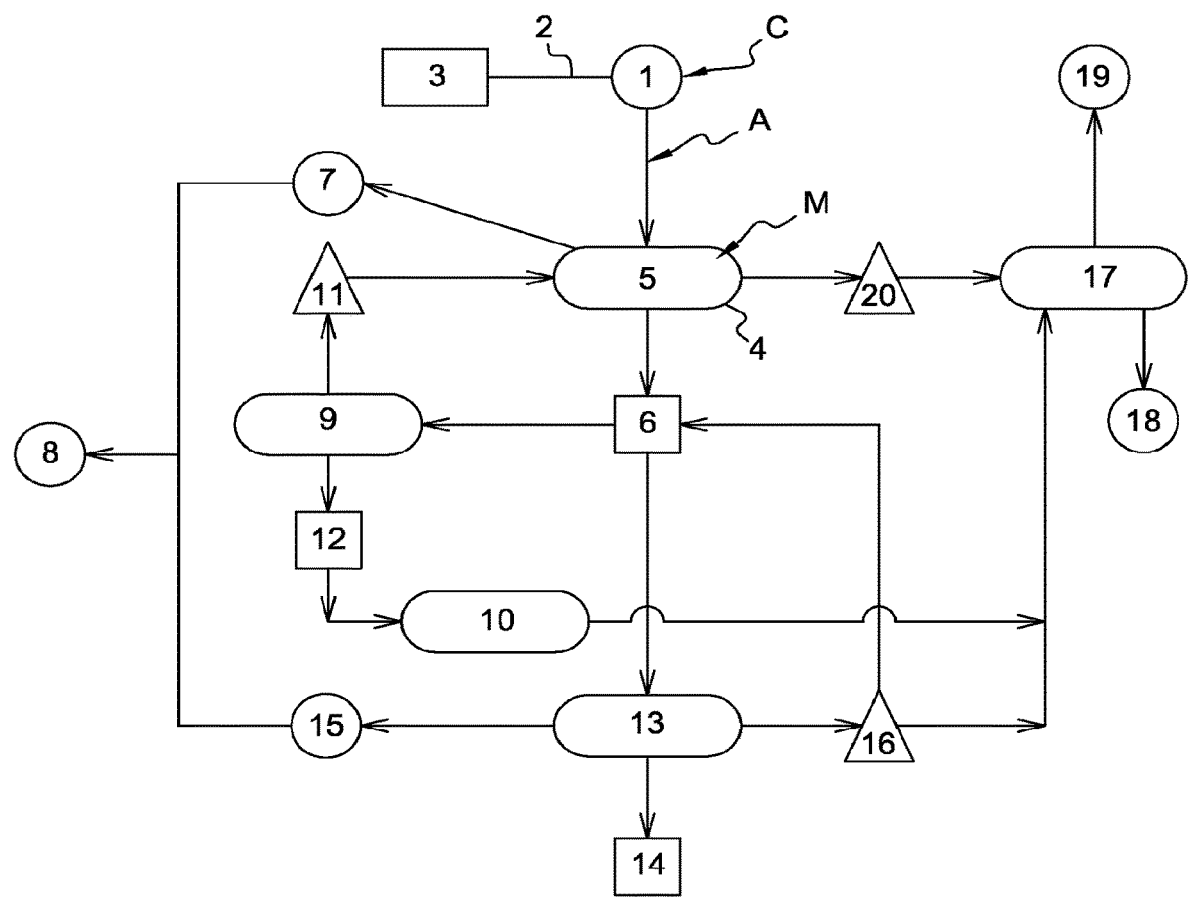

METHOD FOR PRODUCING ORGANIC MOLECULES FROM FERMENTABLE BIOMASS

CROSS REFERENCE TO RELATED APPLICATIONS

This is a National Phase entry of International Application No. PCT/FR2015/051967, filed Jul. 17, 2015, which claims priority to French Patent Application No. 1457198, filed Jul. 25, 2014, the disclosures of which are incorporated by reference in their entireties.

BACKGROUND OF THE INVENTION

The present invention relates to a process for producing molecules from fermentable biomass. This production is carried out from biomass until molecules of interest, that are directly usable, are produced, in a manner similar to a production of molecules in a biorefinery. Here, the process includes an anaerobic fermentation step, among others.

Fermentable biomass here denotes an advantageously but not exclusively non-food organic substrate obtained from waste products, byproducts and coproducts formed by organic matter, that is to say, biomass from human activities whether related to domestic, industrial, agricultural, forestry, aquaculture, agro-industrial activities or livestock farming. As a nonlimiting example, one can cite, as organic substrate, manure, the organic fraction of domestic waste, slaughter house coproducts, cellulosic or ligno-cellulosic residues from the agro-industry, such as those from the transformation of sugar cane (bagasse), sunflower or soybean.

Anaerobic fermentation is understood to mean fermentation carried out under anaerobic conditions by microorganisms, eukaryotes or prokaryotes, such as bacteria, fungi, algae or yeasts.

Here, the term molecule denotes, but nonexclusively, so-called precursor molecules. These precursors subsequently enable the production of other molecules that are more of interest, from an energy production and/or chemistry standpoint, than the precursors, it being understood that they are organic molecules. One can cite, as molecules of interest from an energy production and/or chemistry standpoint, for example, molecules having a carbon chain, such as acids, hydrocarbons, methane, esters, alcohols, amides or polymers.

Today, molecules that are of interest from an energy production and chemistry standpoint are generally derived from fossil raw materials such as hydrocarbons. Their production from renewable raw materials, such as biomass, is thus a solution of interest from an economic and ecological standpoint. Methods for producing a given type of molecules from organic substrate are thus known. One can cite, for example, the production of ethanol, which is an important component of first-generation biofuels for vehicles, derived from biomass, essentially foodstuffs such as maize, wheat, beetroot or sugarcane. Such processes not only produce only one monotype of a recoverable molecule, but a significant portion of the carbon in the substrate is converted into a low-end coproduct, such as carbon dioxide. In addition, the recovery, by various means, of molecules of interest, leads to the production of a large amount of waste, which generates environmental problems. Moreover, the microorganisms used in such processes are usually genetically modified microorganisms. To remedy this, there are known processes that aim to produce so-called precursor molecules by fermentation of the generally pretreated or food biomass. These molecules are then transformed, by known chemical pathways, into various usable molecules. The transformation into final molecules takes place later and independently of the production phase of these so-called precursor molecules.

U.S. Pat. No. 6,043,392 discloses such a process for producing ketones by thermal treatment of volatile fatty acid salts obtained by anaerobic fermentation. A portion of the volatile fatty acids is also converted into hydrocarbons, aldehydes and alcohols. In addition to a limited number of final products obtained by such a process, the process is carried out in two separate steps, namely the fermentation followed by the treatment of the VFA salts. In other words, the process is not continuous. It is known that the production of volatile fatty acids carried out by anaerobic fermentation induces an acidification of the medium that is detrimental to the microorganisms. Since the acidification of the medium induces an inhibition of the microorganisms, and thus a slowing or even a stopping of the fermentation, it is necessary to work discontinuously. For this purpose, the VFAs are extracted after a given fermentation time. U.S. Pat. No. 4,358,537 also discloses an in situ process for producing carbohydrates from a parcel of peat. Here, the VFAs are not a product sought as precursor. Similarly, US-A-2013/309 740 discloses an anaerobic fermentation the purpose of which is the production of methane, the VFAs being a waste product to be eliminated. These processes thus do not enable a rapid and continuous production of so-called precursor molecules, since the yield is not optimal.

Now, in the context of an industrial process for producing molecules by fermentation from biomass, it is important, in order to guarantee the productivity of the installation, to have a process whose yield and adaptability to the production of different molecules are not only as high as possible, but above all regular and controlled while limiting the production of waste and effluents to be treated subsequently. This is all the more important as the organic substrates used as fermentable biomass are mainly of agricultural, industrial, domestic and/or agro-food origin in order to guarantee large volumes. Consequently, there is a great variability, qualitative and quantitative, of the substrate, depending on various factors such as location or season.

SUMMARY OF THE INVENTION

The invention aims more particularly to overcome these disadvantages by proposing a process that makes it possible to produce, in a regular and controlled manner, various so-called biosourced molecules, that is to say molecules from biomass, using a biorefinery approach.

For this purpose, the invention relates to a process for producing organic molecules from fermentable biomass, including an anaerobic fermentation step, said fermentation producing fermentation metabolites referred to as precursors, such as volatile fatty acids, these so-called precursor metabolites being transformed into final organic molecules by non-fermentation means, the process including at least one step consisting in running the fermentation of an organic substrate formed by fermentable biomass in a fermentation reactor until the production, as fermentation metabolites, of volatile fatty acids (VFAs) having a carbon chain of 1 to 8 carbons, characterized in that it includes at least the following steps:

a) extracting, between the start of production and the maximum of production of said volatile fatty acids, at least some of the volatile fatty acids from the fermentation medium so that the production of fermentative metabolites by the microorganisms is not affected, and introducing at least part of the liquid phase containing microorganisms from the extraction into the fermentation reactor, b) synthesizing organic molecules from the fermentation metabolites produced in the fermentation reactor or from the volatile fatty acids extracted in step a), c) continuing steps a) to b) until the final organic molecules, in terms of quantity and quality, are obtained.

Such a process makes it possible to produce fermentative metabolites known as precursors, namely volatile fatty acids, continuously while preserving the population of microorganisms present in the bioreactor. Indeed, the extraction step makes it possible not only to avoid the accumulation of volatile fatty acids in the medium, but also to preserve the microorganisms, the extraction being carried out under non-lethal conditions for all the microorganisms. In other words, the extraction is biocompatible, that is to say that it does not interfere with or degrade the biological medium in which it is carried out. In this manner, one avoids the problems connected with the accumulation of precursors in the reactor, for example, the acidification of the fermentation medium by accumulation of the volatile fatty acids that are harmful to the microorganisms. The activity of the microorganism is kept at a high level, close to the initial level, throughout the fermentation cycle, since most of the microorganisms are not inhibited by this extraction step.

According to advantageous but nonobligatory aspects of the invention, such a process can include one or more of the following features:

before step a), a mixture of microorganisms from defined natural ecosystems is inoculated into the fermentation reactor.

Steps a) to c) are carried out continuously.

The residues from the process are suitable for being used as amendment, fertilizers or as coproduct such as methane.

The invention also relates to an installation for implementing a process according to one of the previous features, characterized in that it includes at least one fermentation reactor, one extraction device suitable for ensuring the extraction of the volatile fatty acids contained in the liquid phase produced during the fermentation, and one synthesis device such as a chemical reactor or an electrolysis cell, suitable for ensuring the synthesis of the fermentation metabolites obtained during the fermentation into final organic molecules.

According to advantageous but nonobligatory aspects, such an installation can include the following features:

It includes at least one device for storing the substrate.

BRIEF DESCRIPTION OF THE DRAWING

The invention will be better understood and more of its advantages will become clearer after reading the description of several embodiments of the invention, given as nonlimiting example and provided in reference to the following drawings in which:

FIG. 1 is a simplified diagram representative of the process that is the subject matter of the invention.

DETAILED DESCRIPTION OF THE INVENTION

The different steps of the process are now described in reference to several embodiments, it being understood that the steps, which are known per se, are not given in detail. In particular, reference will be made below to the diagram of FIG. 1 illustrating an advantageous embodiment of the invention. In particular, the process is described in the case of the continuous fermentation regime. Indeed, the steps pertaining to the startup of the fermentation are known per se.

First of all, the substrate 1 used here is advantageously untreated, that is to say that it has not been subjected to any physicochemical or enzymatic pretreatment. In a variant, the substrate 1 can have been subjected to a mechanical treatment, for example, crushing 2, which facilitates the action of the microorganisms on the substrate. The latter consists mostly of the biomass 3 from human activities. As a non-limiting example, one can cite agricultural or plant waste (straw, bagasse, corn grains, grasses, wood, clippings), paper waste (cardboard, paper), agro-food waste, slaughterhouse waste, the organic fraction of domestic waste, effluents from livestock farming (manure, runoff from feedlots, droppings), algae, aquaculture waste, forestry waste, or fermentable coproducts of the cosmetic industry. In another embodiment, the substrate 1 has been subjected to a physicochemical or enzymatic pretreatment, although this is not a preferred embodiment.

Preferably, but not in a limiting manner, the substrate 1 is used as supplied, provided that its fermentability is preserved. This fermentability is characterized by the methanogenic potential of the biomass, commonly referred to by the English-language acronym BMP (Biochemical Methane Potential). A controlled dehydration, as described in the patent application FR1302119 filed by the applicant, makes it possible to maintain this fermentability over a period of several months.

Certain substrates also contain organic molecules such as organic acids, which will have no influence, or only a marginal influence, on the fermentation process. In contrast, these molecules can be found in the fermentation medium and participate, for example, as precursors, in the production of the final organic molecules.

With certain types of substrate, it can be advantageous to incorporate nutrients and/or mineral compounds in order to increase bacterial growth and/or regulate the pH of the substrate and/or of the coproducts promoting the production of VFAs or of other molecules. As an example, one can cite the addition, in a small amount, of NaOH, KOH, Ca(OH)$_2$, K$_2$HPO$_3$, KH$_2$PO$_3$, of glycerol or of solutions of vitamins or trace elements. This addition is represented by arrow A.

The substrate is introduced into a fermentation reactor 4, which is known per se and dimensioned for the desired production, whether the latter is on a laboratory scale for running tests or on an industrial scale for production. In other words, the fermentation reactor 4 or bioreactor has a volume varying from a few liters to several hundred cubic meters, depending on the needs.

Advantageously, but nonobligatorily, microorganisms are introduced beforehand into the fermentation reactor 4, at least at startup time, in a sufficient amount to initiate the fermentation. Clearly, the quantity of microorganisms introduced depends on the substrate, among others. These microorganisms are inoculated in the form of a consortium, illustrated by arrow M. The term consortium refers to a mixture or a mix of microorganisms, eukaryotes or prokaryotes, which may be bacteria, yeasts, fungi or algae. These microorganisms M come essentially from natural ecosystems suitable for carrying out fermentation under anaerobic conditions. As a nonlimiting example, one can cite, as ecosystems, the anaerobic zone of aquatic environments, such as the anoxic zone of certain lakes, soils, marshes, sewage sludge, the rumen of ruminants, or the intestine of termites. It should be kept in mind that the qualitative and quantitative distribution of the different types and species of microorganisms in the consortium M is not known with precision and, above all, can greatly vary. It turns out that this qualitative and quantitative diversity of the microorganisms surprisingly contributes robustness and adaptability to the fermentation process, making it possible to ensure an optimal use of the substrates, regardless of the composition of the latter, and this under variable fermentation conditions.

Moreover, due to the fact that the substrate 1 is used as is, that is to say that it is not sterilized or, more generally, not rid of the microorganisms that it contains before its introduction into the bioreactor, it is found that these microorganisms endemic to the substrate 1 are in fact incorporated in the consortium M or at least associated with the latter in the bioreactor 4.

Moreover, one observes extensive fluctuation not only between the different consortia of identical origin but also within the same consortium during fermentation. The studies of the inventors (Pessiot et al., Fed-batch Anaerobic Valorization of Slaughterhouse By-products with Mesophilic Microbial Consortia Without Methane Production. Applied Biochemistry and Biotechnology, Jan. 6, 2012) have shown that this fluctuation is due to successive waves of populations of microorganisms, but that these populations are, overall, similar in terms of activity and types of microorganisms, over a given period. Due to this fact, the products of the fermentation are relatively speaking constant, at least qualitatively.

With a view to producing volatile fatty acids, the fermentation 5 presents, according to the process of the invention, interesting features such as the fact of taking place under nonsterile conditions. The consortium M of microorganisms makes it possible to use the substrate 1 in an optimal manner, and without adding products such as enzymes. Moreover, the fermentation 5 takes place under anaerobic conditions, more precisely when the redox potential is less than −300 mV, advantageously between −550 mV and −400 mV, when the pH is lower than 8, preferably between 4 and 7. Thus, the fermentation 5 is advantageously limited to the production of fermentation metabolites referred to as precursors, that is to say of volatile fatty acids or VFAs. Indeed, the goal is to carry out, in a fermentation reactor 4, a reaction similar to the acidosis phenomenon encountered in ruminants, while limiting as much as possible the production of methane which, in general, is one of the final metabolites obtained after the completion of such an anaerobic fermentation.

The fermentation 5 carried out according to the invention with the consortium M makes it possible, in contrast to fermentations with defined strains, to degrade not only the sugars (pentoses, hexoses or others) present in the substrate 1, but also the major proportion of the components of substrate 1, such as proteins, nucleic acids, lipids, and carboxylic acids. Thus, the yield of such a fermentation 5 is particularly high, the production of waste being low. The fermentation of complex molecules such as proteins is of particular interest, since it makes it possible, among other effects, to produce butyric acid, 2-methylbutyric acid, and isovaleric acid. These branched volatile fatty acids are precursors having a high potential for the production of branched molecules such as branched hydrocarbons, which present advantages as fuel. In other words, the fermentation 5 produces, among the different compounds generated, precursors for the synthesis of biofuels and biomolecules that are of interest in chemistry.

More precisely, this fermentation 5 leads, in a first step, to the formation of volatile fatty acids having one to eight carbons, mainly two to four carbons, such as acetic acid, propionic acid, and butyric acid. In addition, volatile fatty acids having a longer chain, that is to say more than four carbons, are obtained, such as valeric acid, caproic acid, heptanoic acid or octanoic acid. By continuing the fermentation and/or increasing the quantity of microorganisms in the bioreactor 4, if necessary with selected microorganisms, it is possible to promote the production of VFAs having a long carbon chain, that is to say more than four carbons. In other words, the metabolites produced in quantity during the fermentation 5 are volatile fatty acids, most of which comprise two to six carbons.

It should be noted that it is also possible to add to the fermentation reactor 4 carboxylic acids having long carbon chains (C8 to C22) which will be fermented or transformed, during subsequent chemical transformation steps, into hydrocarbons such as octane and kerosene. These carboxylic acids can be added, along arrow C, in unprocessed form or via substrates that contain them, such as certain oil-containing plant products. As nonrestrictive examples, one can cite sunflower, soybean, coconut and oil palm, peanut or Jatropha oils. These carboxylic acids or these oils are advantageously incorporated in the substrate 1.

The fermentation 5 can be carried out in discontinuous or batch mode, in continuous-discontinuous or fed-batch mode, or continuously in a single reactor or in several fermentation reactors arranged in series.

The fermentation 5 is carried out by using conventional fermentation techniques for generating anaerobic conditions. For this purpose, the use of a carbon dioxide atmosphere is preferable, even if other gases such as nitrogen or argon can be considered for achieving the anaerobic conditions. The temperature within the fermentation reactor(s) 4 is between 20 and 60° C., preferably between 35 and 42° C. The pH is lower than 8, preferably between 4 and 7. The redox potential is less than −300 mV, advantageously between −550 mV and −400 mV. The means for the management and maintenance of the temperature and of the pH are known per se.

The fermentation 5 is continued long enough to produce volatile fatty acids in the liquid phase, illustrated by reference 6. The fermentation time varies as a function of, among other factors, the substrate 1, the microorganisms M present, the initial VFA concentration, and the fermentation conditions. Typically, the fermentation period is between 1 and 7 days, preferably between 2 and 4 days. The concentration of VFAs 6 obtained in the fermentation medium at the end of this period is variable, but is generally on the order of 10 to 20 g/L, depending on the volatile fatty acids, it being understood that under certain conditions it can be greater than 35 g/L, for example, close to 50 g/L. At the end of the fermentation step, the fermentation medium has an acidic pH, generally between 4 and 6.

Clearly, the fermentation 5 produces other compounds, particularly gases 7, such as carbon dioxide, hydrogen or methane, which, advantageously, are recovered and used in a known manner, according to reference 8.

The carbon dioxide is, for example, reintroduced into the fermentation reactor 4 in order to participate in the maintenance of the anaerobic conditions. In a variant, it is used as carbon source for the production of photosynthetic biomass. Other metabolites are produced, for example, lactic acid, esters, and alcohols. The latter can either be reintroduced into the bioreactor 4 in order to continue the fermentation 5, or be used for other applications as is or after transformation.

The next step is the extraction 9 of the volatile fatty acids 6 so formed. The latter, by reactions that are known per se, will produce, in a subsequent step 10, so-called biosourced molecules, depending on the needs defined. In a variant, as indicated above, they form a substrate for a so-called secondary fermentation in order to produce volatile fatty acids having a longer carbon chain. This fermentation can be carried out in the same reactor, in continuation of the first fermentation, or, in a variant, in another reactor. For example, one can cite the secondary fermentation, by certain microorganisms such as *Megasphaera edelsnii* or *Clostridium kluyveri*, of acetic acid and butyric acid to form caproic acid and caprylic acid. Such a fermentation thus makes it possible to increase the quantities of certain VFAs present initially in a limited quantity.

In all cases, the volatile fatty acids 6 produced in the liquid phase by anaerobic fermentation 5, which are extracted at least in part, are extracted under conditions such that the extraction 9 does not affect, or at least only marginally affects, the production of volatile fatty acids by the microorganisms present in the fermentation medium. When volatile fatty acids are extracted from the fermentation medium, the acidification of the medium by these acids is in fact reduced.

Advantageously, to the extent that the extraction process used is not lethal for all the microorganisms, it is found that the residual liquid phase 11, after the extraction 9, also contains a certain amount of living and thus potentially active microorganisms. Since, in this liquid phase 11, the concentration of volatile fatty acids 6 is less than that of the fermentation medium, it is therefore possible to reinject it into the fermentation reactor 4. Thus, not only are the volatile fatty acids present in the medium diluted during the course of fermentation 5, and the pH of the medium is raised, but the medium is also reinoculated with microorganisms, ensuring the fermentation 5 by extraction 9 of the acid compounds 6.

Such a solution makes it possible to optimize the yield of the fermentation 5 and to carry out fermentation continuously while reducing the reaction times and limiting waste production to nearly zero waste.

The extraction 9 is advantageously carried out in the liquid phase. It is carried out continuously or sequentially, for example, with an extraction every 12 hours. In all cases, the extraction of a portion of the volatile fatty acids is carried out between the start of production and the maximum of production of the metabolites. Advantageously, the extraction is carried out in the vicinity of the inhibition threshold of the microorganisms by the volatile fatty acids. This threshold depends on the substrate and the fermentation conditions, among other factors. Similarly, the introduction of the liquid phase from the extraction is carried out within a time that makes it possible to maintain a high level of production of volatile fatty acids, that is to say close to the level at which the extraction was carried out.

Once extracted 9, the volatile fatty acids 6 are purified 12 and/or transformed, according to the step referenced 10, into other products such as alkanes, alkenes, amides, amines, esters, polymers, using techniques that are known per se, such as distillation, electrosynthesis, esterification, amidation or polymerization.

Concomitantly, in an advantageous variant, a portion of the volatile fatty acids 6 produced during the fermentation 5 is not extracted but subjected to a step of electrosynthesis 13 or synthesis by electrolysis. In this way, hydrocarbons are produced primarily from the volatile fatty acids with a long carbon chain, up to the acetate.

The step of electrosynthesis 13 makes it possible to convert volatile fatty acids 6 produced into large quantities of gaseous and liquid compounds 14 via the known Kolbe and/or Hofe-Moest electrochemical decarboxylation reactions. These two reactions occur simultaneously during the synthesis by electrolysis, but an adjustment to promote one or the other of these reactions is possible, by modifying easily controlled parameters as described below. Various metabolites can be produced by varying these parameters, which enables a flexible production of different molecules, both qualitatively and quantitatively.

The electrosynthesis 13 makes it possible to convert the volatile fatty acids directly in the fermentation medium. Consequently, the electrosynthesis is also a means for extracting the volatile fatty acids from the fermentation medium.

When other organic molecules such as carboxylic acids or alcohols are added to the volatile fatty acids, the range of hydrocarbons and products that can be formed is enlarged.

Surprisingly, the applicant observed that the step of electrosynthesis can be carried out in the fermentation medium, under gentle reaction conditions, at ambient temperature and pressure, at 3 V or more than 3 V, and at 1 mA/cm2 or more than 1 mA/cm2 of current density at the anode, using, for example, electrodes made of platinum or carbon such as, for example, graphite.

Concerning the electrosynthesis conditions, the pH of the aqueous phase containing the volatile fatty acids is between 2 and 11, preferably between 5.5 and 8. Under acidic or neutral pH conditions, the Kolbe reaction supplying alkanes is favored, while under alkaline pH conditions, it is the oxidative deprotonation of the Hofer-Moest reaction supplying alkenes that is favored.

In this step of electrosynthesis 13, the VFAs, that is to say carboxylic acids, with short and medium carbon chains, have to be in the form of carboxylates in order to be used. This is the reason why a low pH will not only tend to decrease the concentration of volatile fatty acids in the form of anions, but also the solubility of the carboxylic acids or VFAs with medium carbon chain. The pH can be adjusted using, among other compounds, soda in order to maintain high concentrations of carboxylates for undergoing the electrolysis. In general, there is no need to use organic solvents, the fermentation media being good electrolytes for the step of electrosynthesis 13.

Organic solvents are needed almost only for the reagents with low solubility in water, such as the carboxylic acids or VFAs with long carbon chains. In the latter case, methanol, ethanol and isopropanol can be solvents of choice. Alternatively, due to their low solubility in an aqueous solution, these carboxylic acids or VFAs with long carbon chains can be easily separated and concentrated in order to be subjected to the electrolysis step in a second phase and lead to high yields of electrolytic products.

To the extent that it is possible, in a nonobligatory variant, to use a divided electrolysis cell, the products formed at the anode and at the cathode, respectively, can be separated easily.

Alternatively, all the compounds obtained by electrosynthesis can be recovered in a single container and separated or transformed subsequently.

In a nonlimiting example, once collected, the gaseous products 15 formed after the completion of the electrosynthesis 13, such as hydrogen, carbon dioxide, alkanes, alkenes, can be compressed and separated by gaseous liquefaction, as indicated above under reference 8.

In another embodiment, it is possible to consider using semiporous membranes in double electrochemical cells in order to separate the two electrodes. Thus, the electrodes can be placed very close to one another in order to prevent electrical arcs.

On the other hand, the products 14 obtained after completion of this step of electrochemical conversion are, among others, mixtures of hydrocarbons, hydrogen and carbon dioxide, which contain no contaminant compared to natural gases from the oil industry, among other products.

In a variant, in order to increase the yields of the synthesis by electrolysis, supplementary techniques are used, such as ultrasound, magnetic fields, alternating current, for example.

After completion of the electrosynthesis 13, the untransformed VFA residues 16 start again, in part, at step 6 in order to be extracted (step 9) and/or to be subjected to a new electrosynthesis (step 13). A portion of the residues 16 is recycled in step 17, that is to say gasified, incinerated or transformed. The fermentation metabolites such as the volatile fatty acids and the residual substrates from the various steps of fermentation 5, extraction 9 or electrosynthesis 13 are methanized (step 17) to produce fertilizers and amendments, combined under reference 18, and biogas 19. In an industrial ecology approach, this methanization step 17 is also applied to a fraction 20 of residues or of unfermented substrates. Thus, energy and heat are produced, typically by cogeneration. This production of energy and heat is, at least in part, used to cover the energy needs of the process.

Thus, the process according to the invention makes it possible to produce, advantageously continuously and at a high yield, carbon-based molecules with minimal loss of initial organic carbon.

The following examples illustrate the implementation of the process which is the subject matter of the invention, using different substrates and fermentation conditions.

Example 1: Discontinuous Fermentation of Slaughterhouse Coproducts in a Bioreactor in a Nonsterile Mode A fermentation reactor or bioreactor with 5 L of useful volume containing an anaerobic culture medium (0.5 g/L $K_2HPO_4$, 0.5 g/L $KH_2PO_4$, 1.0 g/L $MgSO_4$, 0.1 g/L $CaCl_2$, 1 ml/L hemin and 5 ml/L of vitamins) with a concentration of 100 g/L of a mixture of unsterilized slaughterhouse waste (blood, viscera, stercoral matter, meat waste, in a ratio of 1/1/1/2) was inoculated at a temperature of 38° C. under stirring with a consortium of natural microorganisms from anaerobic ecosystems such as the anoxic zone of a hyperoligotrophic lake such as the Lake Pavin. For 1042 hours of fermentation, nine fed-batch operations and 6 additions of nonsterile meat-based substrates (886 g of dry matter in_total) were carried out. During this fermentation, monitoring operations of the liquid phase and gaseous phase metabolites were carried out. The fermentation products of the liquid phase were monitored and analyzed. At the end of fermentation, the fermentation medium contained 16 g/L of total volatile fatty acids. The yield obtained is 0.38 g of total VFAs/g of dry matter added to the reactor. This example should be considered a reference test, since no extraction and/or electrosynthetic chemical synthesis was carried out, in contrast to the process of the invention.

Example 2: Semi-Continuous Fermentation of Organic Fractions of Domestic Waste in a Bioreactor in a Nonsterile Mode Example 1 is repeated with the same culture medium, but using a substrate consisting of the fermentable fraction of the domestic waste with a concentration of 50 g/L of dry matter instead of slaughterhouse waste. In addition, and according to the process of the invention, extractions are carried out on the medium during the course of the fermentation. Here, the fermentation takes place over more than 2000 hours, and several in situ extraction sequences are carried out in the bioreactor. The extraction is of the liquid-liquid type, it being understood that the volatile fatty acids are always produced in the liquid phase and that the solvent used for this example is pentane. These operations made it possible, on the one hand, to decrease the final concentration of total fatty acids with, for example, an extraction wherein the concentration in the reactor changed from 26.8 g/L to 20.1 g/L of total VFAs (23% decrease), thereby making it possible to reduce the acidity of the medium and thus to preserve an optimal activity of the consortium M of microorganisms. The extraction also makes it possible to recover volatile fatty acids which have been used for various chemical syntheses such as the production of esters and of amides.

These operations of in situ extraction operations made it possible to demonstrate the biocompatibility of the process, in other words the sequential recovery of metabolites that are of interest from an energy production and chemistry standpoint, such as volatile fatty acids, from biomass via a process combining fermentation and extraction steps. This biocompatibility is characterized by the number of microorganisms per mL present in the bioreactor, which is determined using the analytical technique of flow cytometry. These results range, for example, between samples collected before and after in situ extraction, from $2.3 \times 10^8$ to $8.0 \times 10^7$ microorganisms/mL in one series of measurements, and from 2.9 to $2.3 \times 10^8$ microorganisms/mL in another series of measurements. This shows that there is a reduction of the population of microorganisms present in the bioreactor, after the extraction of the volatile fatty acids, but that this reduction does not result in mass destruction of the microorganisms. The population of microorganisms is sufficient, quantitatively and qualitatively, for the microorganisms to be active, and so that there is very little or no loss of fermentation activity of the consortium of microorganisms.

In another embodiment, the extraction can be carried out, without irreversible stresses, directly in the fermentation reactor 4. It is possible to carry out a fermentation 5 in a continuous mode with the extraction 9 of the fermentation inhibiting metabolites, that is to say by extracting the volatile fatty acids responsible for the acidosis of the medium progressively as they are produced. In a variant, these extraction operations can be carried out in a second compartment, the latter being located in the bioreactor 4.

The following tests illustrate the step of electrosynthesis from volatile fatty acids as precursors, it being understood that it is necessary to use these volatile fatty acids in carboxylate form during these chemical reactions.

Example A

A 1M sodium acetate solution underwent an electrolysis reaction using graphite electrodes with a current density of 100 $mA/cm^2$. After 180 minutes of reaction, 63% of the initial acetate concentration was consumed. The metabolites obtained in the gaseous phase are hydrogen (350 mL or 15 mmol), carbon dioxide (330 mL or 13.8 mmolC), methane (7 mL or 0.3 mmolC), and ethane (30 mL or 2.51 mmolC). The metabolites obtained in the liquid phase are methyl acetate (66 mg or 0.9 mmol) and methanol (87 mg or 2.7 mmol). The Cmol result (Cmol.Product/Cmol.Substrate) of this reaction is 0.9±0.1. The yields of hydrogen, carbon dioxide, ethane, methane, methyl acetate and methanol are 473 ml/g of acetate, 446 mL/g of acetate, 41 ml/g of acetate, 10 mL/g of acetate, 90 mg/g of acetate, and 118 mg/g of acetate, respectively.

Example B

Example A is repeated, but with 1M sodium propionate as substrate. After 180 minutes, 56% of the initial concentration of propionate was consumed. In the gaseous phase, hydrogen, methane, carbon dioxide, ethene and butane are obtained, and, in the liquid phase, ethanol and ethyl propionate are obtained.

Amidation reactions were also carried out:

Example C: Amidation—Acetate

The amidation reaction is carried out in a reflux setup using a mixture of a biosourced acetic acid solution and an ammonia solution under stoichiometric conditions. The reaction mixture is heated at 80° C. for 4 hours, then the excesses of reagents are eliminated by distillation. The product of the reaction is recrystallized in order to obtain the biosourced acetamide. The yield of the amidation reaction under these conditions is 63%.

Example D: Amidation—Butyrate

Example C is repeated, but with a biosourced butyric acid solution and at a temperature of 90° C. After 5 hours and after recrystallization of the biosourced butyramide, the yield of the amidation reaction is 69%.

Example E: Amidation—VFA Mixture

Example C is repeated, but with a mixture of biosourced volatile fatty acids (acetic acid, propionic acid, butyric acid, isobutyric acid, isovaleric acid, valeric acid, isocaproic acid, caproic acid, heptanoic acid, octanoic acid . . . ) from the extraction phase as described in the preceding examples at a temperature of 85° C. After 6 h, after elimination of the excesses of reagents by distillation, and after recrystallization of the biosourced amides, the yield of the amidation reaction is 74%. The biosourced amides obtained are the amides corresponding to the biosourced carboxylic acids present in the mixture (acetamide, propanamide, isobutyramide, butyramide, isovaleramide, valeramide, isohexanamide, hexanamide, heptanamide and octanamide . . . ).

These amidation reactions which make it possible to produce, from biosourced volatile fatty acids, biosourced amides, can also be produced with substituted amines in order to obtain secondary and tertiary amides.

Esterification reactions were also carried out.

Example F: Esterification of a VFA Mixture

In order to carry out this esterification, an equimolar mixture of biosourced volatile fatty acids obtained after fermentation and extraction (acetic acid, propionic acid, butyric acid, isobutyric acid, isovaleric acid, valeric acid, isocaproic acid, caproic acid, heptanoic acid, octanoic acid, phenylacetic acid, phenylpropionic acid) (2 mL) and ethanol (1.51 mL) is refluxed for 1 h 15. Sulfuric acid (54 µL) is added initially to the reaction medium as catalyst. At the end of the reaction, gas chromatography reveals the presence of the ethyl esters corresponding to the acids present in the initial mixture, that is to say, in the example: ethyl acetate, ethyl propionate, ethyl isobutyrate, ethyl butyrate, ethyl isopentanoate, ethyl pentanoate, ethyl isohexanoate, ethyl hexanoate, ethyl heptanoate, ethyl octanoate, ethyl phenylacetate, and ethyl phenylpropionate. A conversion yield of 69% of the carboxylic acids into esters is obtained.

Thus, it is shown that the fermentation metabolites such as VFAs, namely according to Examples A to F and in a nonlimiting manner, acetic acid, propionic acid, butyric acid, isobutyric acid, isovaleric acid, valeric acid, isocaproic acid, caproic acid, heptanoic acid, octanoic acid, phenylacetic acid and phenylpropionic acid, can be used easily as precursors of final molecules that are of interest from an economic and energy production standpoint, it being understood that these metabolites are produced by fermentation.

Thus, one has an overall process the different steps of which can be carried out in a staggered manner. This term is used to refer to steps that can be repeated at different times and/or at different sites. In other words, the process offers great adaptability and great flexibility of production.

The implementation of such a process involves not only the presence in the installation of at least one fermentation reactor, but also of at least one extraction device, suitable for carrying out step 9 of extraction, and at least one synthesis device, suitable for carrying out the step of electrosynthesis 13, or, in a variant, another chemical step. These devices are known per se, and their numbers and their dimensions are adapted to the type of production.

Such an installation includes, advantageously, devices for storing the substrate 1 and/or the products from the steps of extraction and/or of electrosynthesis and other chemical syntheses. Management and control means, such as temperature sensors, pH probes, are provided.

The invention claimed is:

1. A process for producing volatile fatty acids, which are transformed into final organic molecules by non-fermentation means, from fermentable biomass via anaerobic fermentation, the process comprising:
   a) producing volatile fatty acids having a carbon chain of 1 to 8 carbons in a liquid phase during anaerobic fermentation of an organic substrate, said anaerobic fermentation initiated by introduction of microorganisms to the organic substrate;
   b) extracting a portion of the volatile fatty acids present in a portion of the liquid phase from the liquid phase under conditions that are nonlethal to the microorganisms while anaerobic fermentation is ongoing, and collecting a residual liquid phase after extraction, wherein the residual liquid phase contains a portion of the microorganisms introduced in step a), whereby pH of the liquid phase during fermentation is raised and the microorganisms introduced in step a) remaining in the liquid phase continue anaerobic fermentation of the organic substrate;
   c) reintroducing a portion of the residual liquid phase containing the portion of the microorganisms back into the liquid phase of the anaerobic fermentation of step a) that is ongoing to provide further anaerobic fermentation of the organic substrate;
   d) synthesizing organic molecules from the portion of volatile fatty acids extracted in step b) and synthesizing by electrosynthesis organic molecules from a portion of the volatile fatty acids produced in step a) not extracted in step b); and
   e) repeating steps a)-d) until a maximum amount of the volatile fatty acids are produced from the organic substrate.

2. The process according to claim 1, wherein steps a)-d) are concomitant.

3. The process according to claim 1, wherein, during step d), providing acidic or neutral pH conditions in the liquid phase, at ambient temperature and pressure, favors synthesizing alkanes by electrosynthesis through Kolbe reactions.

4. The process according to claim 1, wherein, during step d), providing alkaline pH conditions in the liquid phase, at ambient temperature and pressure, favors synthesizing alkenes by electrosynthesis through Hofer-Moest reactions.

5. The process according to claim 1, wherein, before step a), a fermentation reactor is inoculated with a mixture of microorganisms suitable for carrying out the anaerobic fermentation.

6. The process according to claim 1, wherein steps a)-e) are carried out continuously.

7. The process according to claim 1, wherein residues from the process are suitable to produce amendment.

8. The process according to claim 1, wherein the electrosynthesis of step d) occurs in the liquid phase while the portion of the volatile fatty acids and the portion of the microorganisms introduced in step a) are extracted in step b).

9. The process according to claim 1, wherein residues from the process are suitable to produce fertilizers.

10. The process according to claim 1, wherein residues from the process are suitable to produce biogas.

* * * * *